(12) United States Patent
Meador et al.

(10) Patent No.: US 6,234,973 B1
(45) Date of Patent: May 22, 2001

(54) IMPLANTABLE MEDICAL DEVICE FOR SENSING ABSOLUTE BLOOD PRESSURE AND BAROMETRIC PRESSURE

(75) Inventors: John T. Meador, Half Moon Bay, CA (US); Keith A. Miesel; Louis E. Halperin, both of St. Paul, MN (US); Robert T. Taepke, II, Coon Rapids, MN (US); Lee Stylos, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/442,855

(22) Filed: Nov. 18, 1999

Related U.S. Application Data

(62) Division of application No. 09/070,310, filed on Apr. 30, 1998, now Pat. No. 6,024,704.

(51) Int. Cl.[7] .......................................................... A61B 5/02
(52) U.S. Cl. ............................................. 600/486; 128/899
(58) Field of Search ........................... 600/301, 483–486, 600/509; 128/899, 903; 607/2, 9, 18, 27

(56) References Cited

U.S. PATENT DOCUMENTS

| | | | |
|---|---|---|---|
| 5,564,434 | * | 10/1996 | Halperin et al. ........................ 600/486 |
| 5,810,733 | * | 9/1998 | Halperin et al. ........................ 600/486 |
| 5,904,708 | * | 5/1999 | Goedeke ................................ 607/18 |

* cited by examiner

Primary Examiner—Cary O'Connor
Assistant Examiner—Ryan Carter
(74) Attorney, Agent, or Firm—Michael B. Atlass; Harold R. Patton

(57) ABSTRACT

An implantable barometric pressure sensor coupled with an implantable medical device (IMD) provides a barometric pressure related, reference pressure value for use in combination with an absolute pressure value measured by an implantable absolute pressure sensor coupled to the IMD. In one embodiment, the barometric pressure sensor is implanted under the skin and subcutaneous tissue layer at or near the implant site of the IMD. In variations of this embodiment, the barometric pressure is formed as part of a connector module of the IMD or extends from the connector module. In a further embodiment, a percutaneous access device is provided which is adapted to be implanted to extend through the skin and subcutaneous tissue layer of the patient and is coupled with the barometric pressure sensor to provide for an air chamber extending between the atmosphere and the barometric pressure sensor. The barometric pressure sensor is preferably enclosed within an air chamber of the implantable medical device, and a catheter extends between the air chamber of the implantable medical device and the percutaneous access device. Or the barometric pressure sensor is enclosed within an air chamber of the percutaneous access device, and a lead extends between the barometric pressure sensor and the implantable medical device.

2 Claims, 13 Drawing Sheets

IMPLANTABLE MEDICAL DEVICE FOR SENSING ABSOLUTE BLOOD PRESSURE AND BAROMETRIC PRESSURE

CROSS-REFERENCE TO RELATED APPLICATION

This application is a divisional application of U.S. patent appln. Ser. No. 09/070,310 filed Apr. 30, 1998 entitled "Implantable Medical Device for Sensing Absolute Blood Pressure and Barometric Pressure", now U.S. Pat. No. 6,024,704.

Reference is hereby made to commonly assigned, co-pending U.S. Patent Application Serial No filed on even date herewith BAROMETRIC PRESSURE SENSOR FOR USE WITH IMPLANTABLE ABSOLUTE PRESSURE SENSOR by Robert T. Taepke.

FIELD OF THE INVENTION

The present invention relates to an implantable barometric pressure sensor coupled with an implantable medical device (IMD) for providing a barometric pressure related, reference pressure value for use in combination with an absolute physiologic pressure value, e.g. a cardiac pressure value, measured by an implantable absolute pressure sensor coupled to the IMD, and particularly to the fabrication of various embodiments of the barometric pressure sensor and the periodic calibration thereof.

BACKGROUND OF THE INVENTION

A great many IMDs for cardiac monitoring and/or therapy comprising sensors located in a blood vessel or heart chamber coupled with an implantable monitor or therapy delivery device have been proposed or implemented. For example, such cardiac systems include implantable heart monitors and therapy delivery devices including pacemakers, cardioverter/defibrillators, heart pumps cardiomyostimulators, ischemia treatment devices, and drug delivery devices. Most of these cardiac systems include electrodes for sensing and sense amplifiers for recording and/or deriving sense event signals from the intracardiac or remote electrogram (EGM). In current cardiac IMDs providing a therapy, the sense event signals are utilized to control the delivery of the therapy in accordance with an operating algorithm and at least selected EGM signal segments and sense event histogram data or the like are stored in internal RAM for telemetry out to an external programmer at a later time. In the MEDTRONIC® Reveal™ implantable loop recorder, a 42 minute segment of EGM is recorded when the patient feels the effects of an arrhythmic episode and activates the recording function by applying a magnet over the site of implantation, but this device provides no therapy.

Efforts have also been underway for many years to develop implantable physiologic signal transducers and sensors for temporary or chronic use in a body organ or vessel usable with such IMDs for monitoring a physiologic condition other than or in addition to the EGM to derive and store data and/or to control a therapy delivered by the IMD. A comprehensive listing of implantable therapy delivery devices are disclosed in conjunction with implantable sensors for sensing a wide variety of cardiac physiologic signals in U.S. Pat. No. 5,330,505, incorporated herein in its entirety by this reference.

Blood pressure and temperature signal values respond to changes in cardiac output that may be caused by a cardiac failure, e.g., fibrillation or high rate tachycardia, or that may reflect a change in the body's need for oxygenated blood. In the former case, monitoring of a substantial drop in blood pressure in a heart chamber, particularly the right ventricle, alone or in conjunction with an accelerated or chaotic EGM, was proposed more than thirty years ago as an indicia of fibrillation or tachycardia sufficient to trigger automatic delivery of defibrillation or cardioversion shock. More recently, it has been proposed to monitor the changes in blood pressure (dP/dt) that accompany normal heart contraction and relaxation and blood pressure changes that occur during high rate tachycardia and fibrillation or flutter.

A number of cardiac pacing systems and algorithms for processing the monitored mean and dP/dt blood pressure have been proposed and, in some instances employed clinically, for treating bradycardia. Such systems and algorithms are designed to sense and respond to mean or dP/dt changes in blood pressure to change the cardiac pacing rate in a rate range between an upper and a lower pacing rate limit in order to control cardiac output. Similarly, a number of cardiac pacing systems have been proposed, e.g., the system disclosed in U.S. Pat. No. 4,436,092, incorporated herein by reference, and, in some instances employed clinically, that sense and respond to changes in blood temperature to change the cardiac pacing rate in a rate range between an upper and a lower pacing rate limit in order to control cardiac output.

With respect to cardiac monitoring, it has been proposed to sense and record such additional physiologic signals including blood pressure in or adjoining blood vessels and heart chambers during the cardiac cycle, blood temperature, blood pH, to and a variety of blood gases. Implantable heart monitors and blood pressure and temperature sensors that derive absolute blood pressure signals and temperature signals are disclosed in commonly assigned U.S. Pat. Nos. 5,368,040, 5,535,752 and 5,564,434, and in U.S. Pat. No. 4,791,931, all incorporated by reference herein.

The leads and circuitry disclosed in the above-incorporated, commonly assigned, '752 and '434 patents can be employed to record the EGM and absolute blood pressure values for certain intervals. The recorded data is periodically telemetered out to a programmer operated by the physician in an uplink telemetry transmission during a telemetry session initiated by a downlink telemetry transmission and receipt of an interrogation command.

Certain of the measured physiologic signals derived from the heart or blood in the circulatory system are affected by ambient conditions that cannot be separately measured by the above-described IMDs and physiologic sensors. Specifically, blood pressure and temperature signal values derived by a wholly implantable system are affected by atmospheric pressure acting on the patient and ambient temperature or by a fever afflicting the patient, respectively. In addition, certain implantable blood pressure sensors, e.g., those disclosed in the above-incorporated, commonly assigned '434 and '752 patents, are also affected by blood temperature changes Changes in ambient conditions other than weather changes can also influence the measurement of absolute blood pressure changes, including both mean or average blood pressure and dP/dt pressure changes, by implantable pressure sensors. For example, when a patient in which such an implantable blood pressure sensing medical device is implanted changes elevation by ascending or descending in an elevator in a tall building or in an airplane, the change in barometric pressure changes the absolute blood pressure sensed in the body by an amount that can mask changes that are sought to be measured. In the context of an implantable rate responsive pacemaker operating under a rate control algorithm, the pressure change caused by the elevation change itself may exceed the blood pressure change that reflects a change in exercise level of the patient and be mis-interpreted as meriting a change in pacing rate to the upper or lower pacing rate limit, which can, at least, be uncomfortable to the patient. The barometric pressure effect can similarly have a negative effect on operating and detection functions of other IMDs reliant on accurately sensing cardiac blood pressure changes that truly reflect a cardiac function or requirement for cardiac output.

The effect of barometric pressure on cardiac blood pressure measurements has been noted. In commonly assigned U.S. Pat. No. 4,407,296, a micro-machined pressure sensor is disposed at the distal end of a lead in an oil filled chamber on one side of a pressure sensor element that is closed by a flexible membrane that is perpendicular to the lead body axis. The membrane is disposed behind a protective grill at the distal tip of the lead within which blood fluids can contact the exposed side of the membrane. Blood pressure changes deflect the membrane, and the deflection is transmitted through the oil to the micro-machined pressure sensor element which is deflected to produce a pressure signal value change proportional to the blood pressure change acting on the membrane. The blood pressure change reflects both the blood pumping action of the heart and the ambient atmospheric pressure acting on the patient's body. In a first embodiment, the affect of atmospheric pressure is attempted to be offset by providing a chamber behind the sensor element that is sealed at a known average atmospheric pressure. In practice, this approach has proven to be inadequate because the known pressure has accounted adequately for changes in barometric pressure and renders the blood pressure measurements ambiguous.

In a second embodiment, the chamber behind the sensor element is filled with oil and extends proximally through a lumen of the lead body to a further membrane or diaphragm near the proximal end of the lead body that is to be positioned in the subcutaneous cavity under the patient's skin where the implantable monitor or pulse generator is implanted. In this case, the membrane on the lead body is difficult to manufacture, fragile and can become obstructed in chronic implantation. Moreover, the oil filled lumen can be generally either vertical or horizontal in all or in part depending on a number of factors, including the implantation path of the lead body between the subcutaneous cavity and the implantation site of the pressure sensor in the patient's heart chamber and whether the patient is upright or supine. The weight of the oil in the oil filled lumen depends on the orientation of the lumen with respect to the force of gravity, and the variable weight itself biases the pressure sensor element in a variable manner. Therefore, the reference pressure varies unpredictably and may not represent barometric pressure.

In recognition of these problems with absolute pressure sensors employed to measure blood pressure in a heart chamber or blood vessel, it is suggested in the above-incorporated, commonly assigned, '752 and '434 patents that the patient be provided with a belt worn, external pressure recorder that records and time stamps recordings of barometric pressure that can be retrieved and used as reference pressure data for comparison with the internally recorded absolute blood pressure data. Such an externally worn, barometric pressure recorder is intended to be used with implantable hemodynamic recorders and monitoring IMD's. The reference pressure recordings that are periodically stored in the memory of the external device are read out at the time that the absolute pressure data stored in the implantable monitor is telemetered out. The reference values are subtracted from the absolute values to derive the relative pressure values.

Despite the considerable effort that has been expended in designing such IMDs and associated sensors for sensing such physiologic signals, a need exists for a system and method for accounting for ambient conditions surrounding the patient that affect the sensed and measured physiologic signal values, particularly in the case of pressure, e.g., cardiac blood pressure, other fluid pressures in the body, and optionally temperature.

SUMMARY OF THE INVENTION

It is therefore an object of the present invention to provide a system and method employed in an IMD for deriving reference and absolute physiologic signal values employing implantable physiologic sensors to derive relative physiologic signal values for storage and/or control of a therapy provided by the IMD.

It is another object of the present invention to provide a system and method for combining other absolute physiologic signal values with ambient signal values affecting the sensed absolute physiologic signal value to derive relative physiologic signal values for storage and/or control of a therapy provided by an implantable monitor or therapy delivery device.

It is yet another object of the present invention to provide such reference pressure and/or temperature sensors in close association with the IMD intended to be implanted subcutaneously in close relation to the patient's skin for deriving a reference pressure and/or temperature signal value that closely reflects barometric pressure and/or ambient or systemic temperature of a patient.

Moreover, it is an object of the present invention to provide for the calibration of the reference pressure and/or temperature sensor in relation to an external, calibrated, barometric pressure and/or body temperature sensor.

These objects are realized in an implantable system and method of operation thereof for deriving relative physiologic signal value data for use by and/or storage within an implantable medical device implanted within a patient's body comprising the means for and steps of: implanting an ambient state or condition monitoring device under the skin and subcutaneous tissue layer of the patient's body, and with the implanted ambient state or condition monitoring device, sensing an ambient state or condition outside the body affecting a sensed physiologic state or condition within the body; deriving a reference signal value from the sensed ambient state or condition; and conveying the reference signal value to the implantable medical device; implanting a physiologic state or condition monitoring device in relation with a body organ, and with physiologic state or condition monitoring device, sensing a physiologic state or condition within the body of the patient; deriving an absolute physiologic signal value from the sensed physiologic state or condition; and conveying the absolute physiologic signal value to the implantable medical device; and combining the conveyed absolute physiologic signal value and ambient signal value to derive a relative physiologic signal value therefrom.

It is a particular object of the present invention to provide a system and method for combining absolute cardiac pressure and barometric pressure signal values to derive relative cardiac pressure signal values for storage and/or control of a therapy provided by an implantable cardiac monitor or therapy delivery device.

It is a further particular object of the present invention to provide an IMD monitoring system and method for accurately measuring absolute blood pressure and/or temperature at a location within the cardiovascular system and for measuring ambient pressure and/or temperature at a location in the patient's body outside the cardiovascular system and for deriving relative blood pressure and/or temperature signal values therefrom for storage in implantable medical device memory and/or for controlling delivery of a therapy by the IMD.

These and other objects of the invention are realized in the provision and use of an implantable barometric pressure sensor coupled with an IMD that provides a barometric pressure related, reference pressure value for use in combination with an absolute pressure value measured by an implantable absolute pressure sensor coupled to the IMD. In one embodiment, the barometric pressure sensor is implanted under the skin and subcutaneous tissue layer at or near the implant site of the IMD. In variations of this embodiment, the barometric pressure is formed as part of a connector module of the IMD or extends from the connector module, or is otherwise physically mounted in a fixed relationship to the IMD housing or can. In a further embodiment, a percutaneous access device is provided which is adapted to be implanted to extend through the skin and subcutaneous tissue layer of the patient and is coupled with the barometric pressure sensor to provide for an air chamber extending between the atmosphere and the barometric pressure sensor. The barometric pressure sensor is preferably enclosed within an air chamber of the implantable medical device, and a catheter extends between the air chamber of the implantable medical device and the percutaneous access device. Or the barometric pressure sensor is enclosed within an air chamber of the percutaneous access device, and a lead extends between the barometric pressure sensor and the implantable medical device.

In accordance with a further aspect of the invention, means are provided for periodically calibrating the barometric pressure signal values to account for the effect of fluid pressure at the site of implantation that may change from time to time.

The practice of the present invention in the context of an implantable physiologic monitor advantageously eliminates the need to make time based comparisons of the external ambient signal values continuously stored in a patient worn sensor module with the absolute physiologic signal values uplink telemetered from the implantable physiologic monitor. In the present invention, the relative physiologic signals are already derived and stored so that there is no need to make the time comparisons and correlate two sets of data from the implantable medical device and the externally worn sensor module either manually or using a further correlation device. The present invention is particularly advantageously employed to adjust the absolute pressure values derived from the implantable blood pressure sensor and stored in the implantable monitor.

In the context of the implantable therapy delivery device, the present invention advantageously derives the relative physiologic signal values that more accurately reflect the state or condition of the body organ or part to be treated by the therapy. In the case of a cardiac therapy device dependent on cardiac blood pressure, the relative blood pressure values more accurately reflect cardiac output and are more reliably usable than absolute blood pressure values which can change substantially with changes in weather and elevation of the patient.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS OF THE INVENTION

Figure 1:
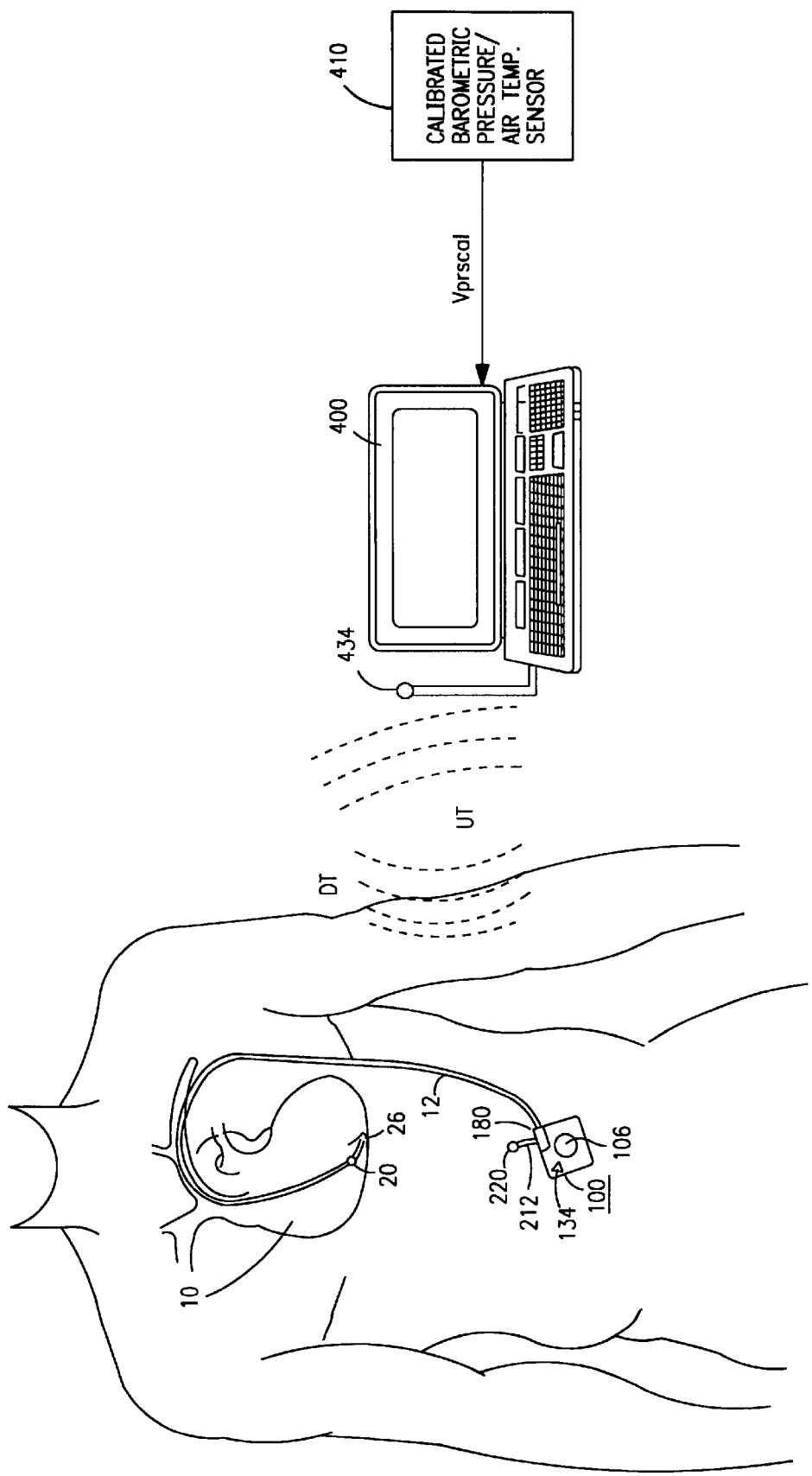
FIG. 1 is a schematic illustration of an IMD coupled to a reference physiologic sensor and an absolute physiologic sensor and the uplink and downlink telemetry communication between an IMD and an external monitor/programmer employed to program and interrogate the IMD and to calibrate the implanted reference physiologic sensor in accordance with the method illustrated in FIG. 5.

FIG. 1 schematically illustrates an IMD 100 coupled with an implanted physiologic sensor 20 for sensing an absolute physioliogic signal value and with an implanted reference physiologic sensor 220 for sensing a reference physiologic signal value, the IMD 100 recording such signal values or a relative physiologic signal values derived therefrom. FIG. 1 also schematically illustrates the relation and telemetry communication between the IMD 100 and an external monitor or programmer 400 coupled with a calibrated physiologic sensor 410 for periodically calibrating the sensed reference physioliogic signal values in accordance with the method illustrated in FIG. 5. The physiologic sensor 20 may take any of the known forms for sensing blood pressure, blood temperature, blood gas components, or the like.

In a preferred embodiment, the physiologic sensors 20 and 220 sense absolute blood pressure and temperature and barometric pressure and body temperature, respectively, and the calibrated physiologic sensor 410 senses barometric pressure and body temperature or just barometric pressure. The physiologic sensor 20 is located on lead 12 just proximal to a lead distal tip fixation mechanism 30 for fixing the physiologic sensor 20 in position despite continuous movement of the heart 10. In the preferred embodiment illustrated in FIG. 2, the lead 12 and physiologic sensor 20 correspond to those disclosed in detail in the above-incorporated, commonly assigned, '434 and '752 patents for deriving absolute blood pressure and temperature signals, but other sensors could be employed.

Figure 2A:
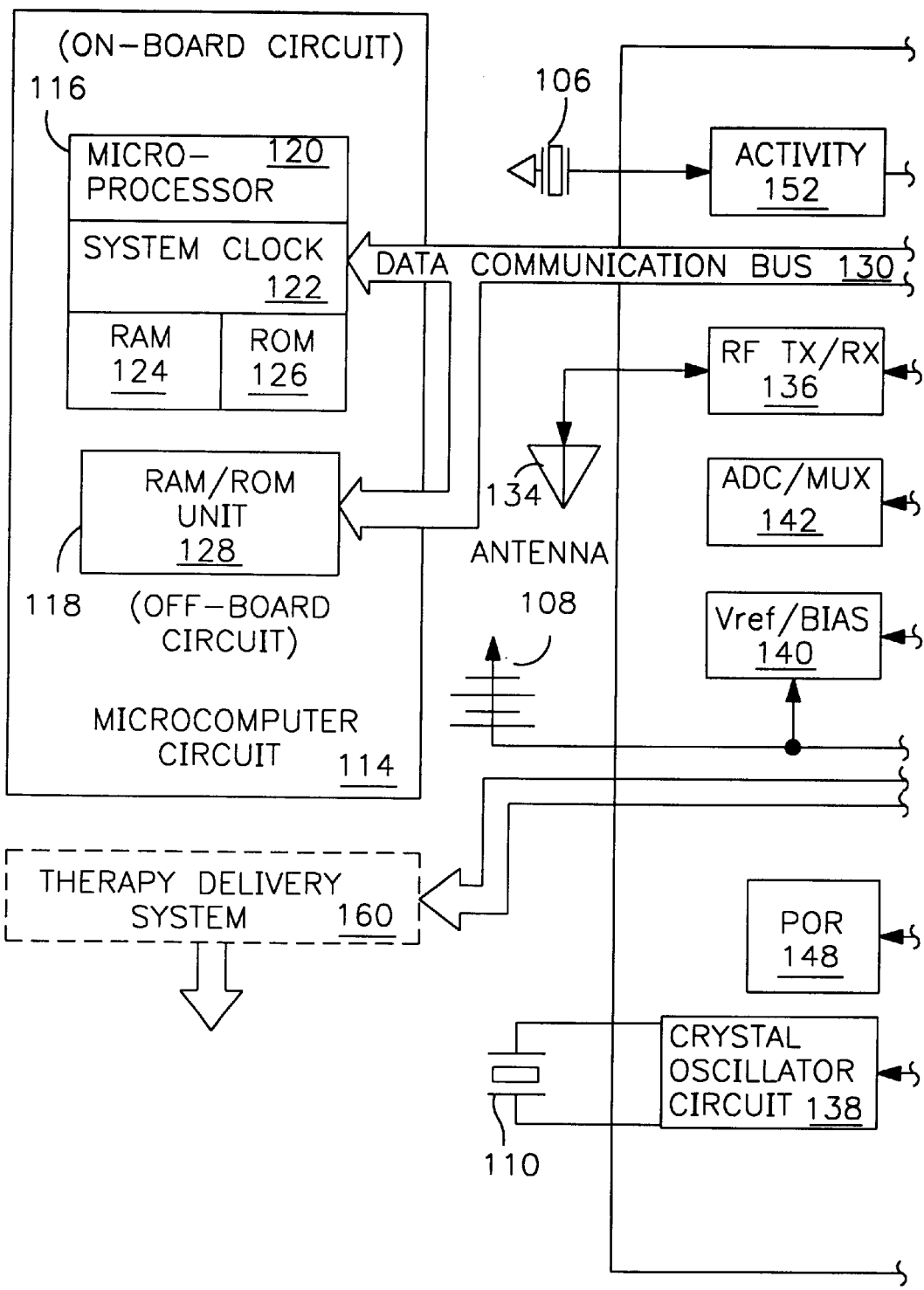
FIG. 2 is block diagram of an exemplary IMD coupled with reference and absolute physiologic sensors as illustrated in FIG. 1 usable as an implantable monitor or as a therapy delivery system.
Figure 2B:
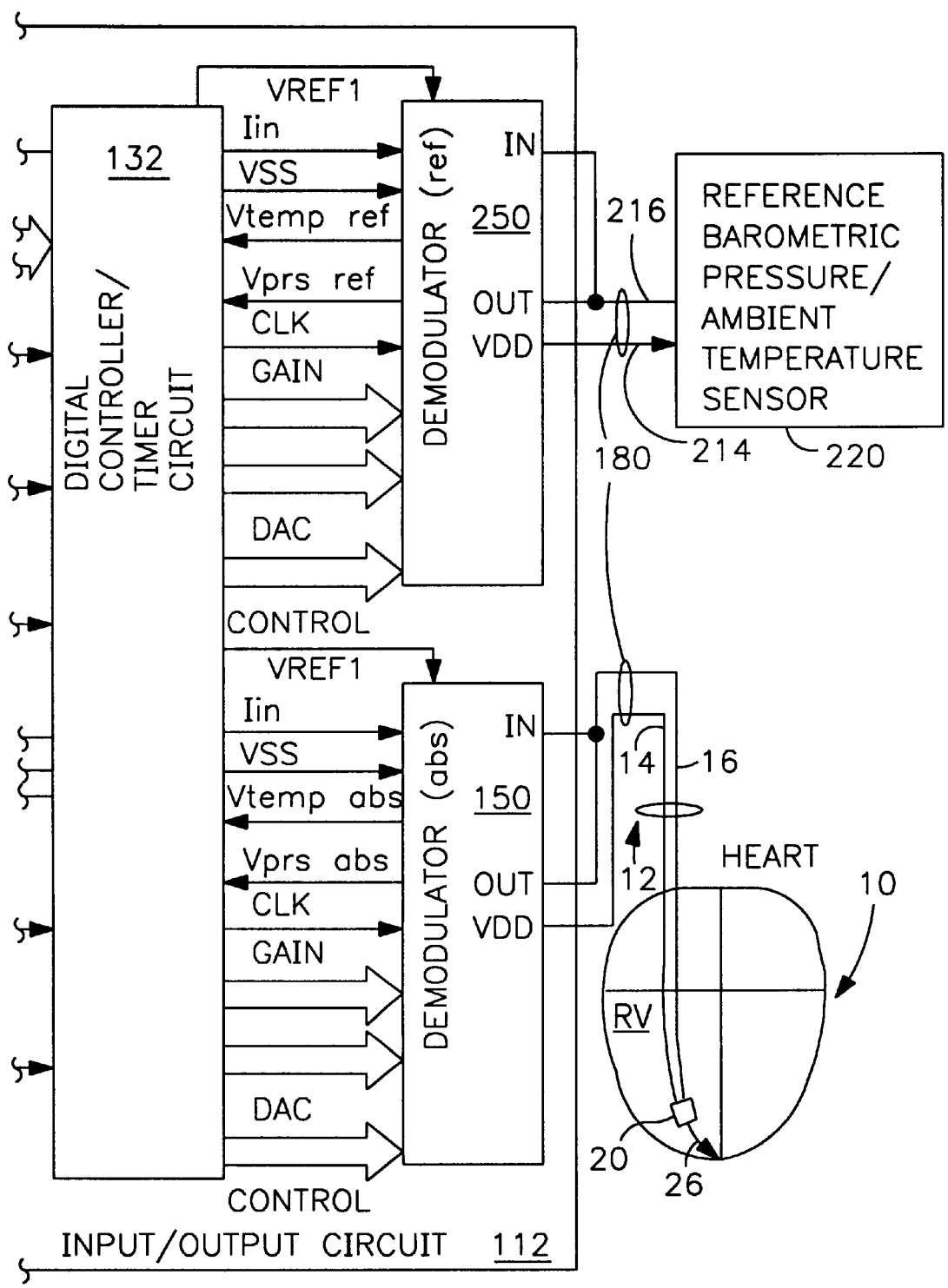

The IMD 100 is depicted implanted in the abdomen of the patient, and it is coupled at its connector module 180 to a lead 12 extending through blood vessels into the right ventricle of the patient's heart 10. The IMD 100 is also depicted as optionally including an activity sensor 106 that is coupled to an activity signal processing circuit as shown in FIG. 2 and described further below. It will be understood from FIG. 3 that when the IMD 100 includes a cardiac therapy delivery device or function, that additional leads or catheters used in the delivery of the particular therapy extend from the connector module 180 to the heart 10.

Such an IMD 100 that provides a therapy and/or monitors a physiologic condition or state is programmable and/or can be interrogated by an external programmer through the use of bi-directional RF telemetry that exchanges data and commands via uplink and downlink RF telemetry transmissions UT and DT through the patient's skin. Thus, the RF telemetry antenna 134 depicted schematically in FIG. 1 is typically enclosed within the IMD housing or in or on the connector module 180 although it can extend from the connector module 180 of the IMD 100. The uplink and downlink telemetry transmissions UT and DT are initiated by use of the external programmer 400 by the physician.

A great many telemetry schemes have been employed and proposed by the assignee, Medtronic, Inc., that typically involve short range telemetry transmissions employing a 175 kHz RF carrier and close physical coupling of magnetic fields encompassing the RF telemetry antenna 134 of the IMD 100 and an external RF telemetry antenna 434 usually located in a programming head placed against the patient's skin. A great many other telemetry systems have been proposed to achieve longer range, yet secure, RF telemetry between implantable and external monitoring devices as described, for example, in U.S. Pat. No. 5,113,869 and in commonly assigned U.S. patent application Ser. No. 08/900,624 filed Jul. 25, 1997, for IMD MICROSTRIP TELEMETRY ANTENNA in the names of Weimin Sun et al., both incorporated herein by reference. The RF telemetry system preferably operates at a long range of about 2 meters or more in a relatively high frequency range. For convenience of description, the preferred embodiment is described as follows using long range RF telemetry transmission, but the invention and following claims are not be interpreted as so limited. Similarly, the terms "telemeter", "telemetry transmission" and the like are intended to embrace any such action and manner of conveying data and commands between the IMD and external monitoring devices or programmers.

In the context of an implantable physiologic monitor, the relative and, optionally, the absolute and/or ambient physiologic signal values are stored in memory for telemetry out to the external medical device (EMD) or programmer 400 in an uplink RF telemetry transmission UT initiated by medical personnel operating the external programmer 400 generating and transmitting an interrogation command via a downlink telemetry transmission DT. In the case where the IMD 100 is an implantable therapy delivery device, the relative physiologic signal values are also employed in therapy delivery algorithms to control the delivery of the therapy. The present invention is preferably implemented in a system as depicted in FIG. 1 operating in accordance with the flow chart of FIG. 4 to deliver a therapy and/or monitor a physiologic condition comprising relative blood pressure and/or temperature as described as follows. However, the principles of the present invention are applicable to the derivation of other relative physiologic signals.

FIG. 2 is a simplified block diagram of the major circuit and hardware components of an exemplary IMD 100 and associated cardiac lead 12 positioning the absolute physiologic sensor 20 in relation to a patient's heart 10. The configuration of the IMD 100 as a therapy delivery device is indicated by the optional therapy delivery system 160 (shown in broken lines) of one of the types depicted in FIG. 3 and described below. The IMD 100 generally includes a microcomputer circuit 114 coupled through a data communication bus 130 with an input/output circuit 112, a battery 108, the optional activity sensor 106, the telemetry antenna 134, the lead 12, a timing crystal 110, a reference physiologic sensor 220, and an optional therapy delivery system 160 The input/output circuit 112 includes the digital controller/timer circuit 132 and the associated components including the crystal oscillator 138, power-on-reset (POR) circuit 148, Vref/BIAS circuit 140, ADC/MUX circuit 142, RF transmitter/receiver (TX/RX) circuit 136, optional activity circuit 152, an absolute physiologic signal demodulator 150, and a reference physiologic signal demodulator 250. Data transmission to and from the external programmer 400 of FIG. 1 is accomplished by means of the telemetry antenna 134 and the associated RF TX/RX circuit 136, which serves both to demodulate received downlink RF telemetry transmission DT and to transmit uplink RF telemetry transmission UT.

Crystal oscillator circuit 138 and crystal 110 provide the basic timing clock for the digital controller/timer circuit 132. Vref/BIAS circuit 140 generates stable voltage reference Vref and current levels from battery 108 for the circuits within the digital controller/timer circuit 132, and the other identified circuits including microcomputer 114, demodulators 150 and 250 and optional therapy delivery system 160. Power-on-reset (POR) circuit 148 responds to initial connection of the circuitry to the battery 108 for defining an initial operating condition and also resets the operating condition in response to detection of a low battery voltage condition. Vref/BIAS circuit 140, analog-to-digital converter and multiplexor (ADC/MUX) circuit 142, POR circuit 148, crystal oscillator circuit 138 and optional activity circuit 152 may correspond to any of those presently used in currently marketed, implantable cardiac pacemakers.

The digital controller/timer circuit 132 includes a set of timers and associated logic circuits connected with the microcomputer 114 through the data communications bus 130. Microcomputer 114 contains an on-board chip including microprocessor 120, associated system clock 122, and on-board RAM and ROM chips 124 and 126, respectively. In addition, microcomputer 114 includes an off-board circuit 118 including separate RAM/ROM chip 128 to provide additional memory capacity. Microprocessor 120 is interrupt driven, operating in a reduced power consumption mode normally, and awakened in response to defined interrupt events, which may include the periodic timing out of data sampling intervals for storage of monitored data, the transfer of triggering and data signals on the bus 130 and the receipt of programming signals. A real-time clock and calendar function may also be included to correlate stored data to time and date. In a further variation, provision may be made for the patient to initiate storage of the monitored data through an external programmer or a reed switch closure when an unusual event or symptom is experienced. The monitored data may be related to an event marker on later telemetry out and examination by the physician.

Microcomputer 114 controls the operating functions of digital controller/timer 132, specifying which timing intervals are employed, and controlling the duration of the various timing intervals, via the bus 130. The specific current operating modes and interval values are programmable. The programmed-in parameter values and operating modes are received through the antenna 134, demodulated in the RF TX/RX circuit 136 and stored in RAM/ROM chip 128.

The lead 12 has first and second lead conductors 14 and 16 extending from the connector module 180 to the absolute physiologic sensor 20 disposed near the distal fixation mechanism 30. The proximal end of lead 12 is formed as a conventional bipolar, in-line pacing lead connector and is coupled to the connector module 180 which is formed as a conventional bipolar, in-line, pacemaker pulse generator connector block assembly of the type shown in FIGS. 6–8 and described below. The second lead conductor 16 is coupled to both the IN and OUT terminals of the absolute signal demodulator 150, and the first lead conductor 14 is coupled to the VDD terminal of the absolute signal demodulator 150 through the connection of the lead connector and the connector module 180.

In the preferred embodiment, the absolute physiologic sensor 20 is an absolute blood pressure and temperature sensor which develops both blood pressure and temperature time-modulated intervals that are decoded as absolute blood pressure and temperature signal values in an absolute signal demodulator 150. The sensor 20 is formed with a flexible diaphragm 40 that forms one plate of a variable pickoff capacitor and a fixed reference capacitor. Deflection of the diaphragm 40 in response to blood pressure changes causes the variable pickoff capacitance to change, and the capacitance change is detected by a signal modulating circuit described in detail in the above-incorporated, commonly assigned, '434 and '752 patents.

The reference physiologic sensor 220 preferably corresponds in material respects to the construction of the absolute physiologic sensor 20 or if not, develops a usable reference physiologic signal value that can be combined with the absolute physiologic signal value to derive an accurate relative physiologic signal value. In this embodiment, the reference physiologic sensor 220 preferably is a reference barometric pressure and/or ambient temperature sensor 220 constructed in the manner described in detail in the above-incorporated, commonly assigned, '434 and '752 patents having a diaphragm 240 that deflects with changes in barometric pressure. Therefore, the reference physiologic sensor 220 develops both blood pressure and temperature time-modulated intervals that are decoded as reference blood pressure and temperature signal values in an reference signal demodulator 250 that is also described in detail in the above-incorporated '434 and '752 patents.

Figure 6:
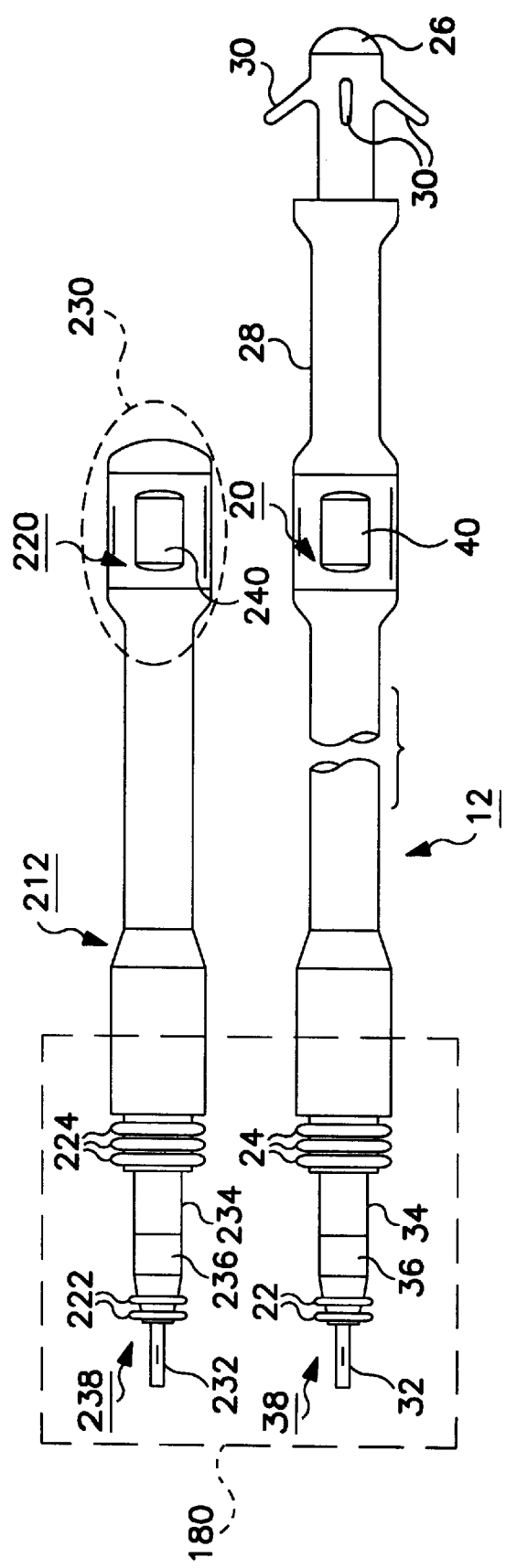
FIG. 6 is a plan view of both reference and absolute blood pressure and/or temperature sensor bearing leads adapted to extend from the connector module of the IMD of FIGS. 1 and 2.

It will be understood from the following description that the reference physiologic sensor 220 is located either at the end of a short lead body 212 extending from a bore of the connector module 180 (as shown in FIGS. 1 and 6 and described further below) or is located in or otherwise extends from the connector module 180. In the former case, first and second conductors 214 and 216 are within the short lead body 212. In the latter case, the first and second conductors 214 and 216 are coupled with feedthrough pins extending into the hermetic seal housing or can of the IMD In either case, first and second conductors 214 and 216 extend from the VDD terminal and both the IN and OUT terminals, respectively, of the reference signal demodulator 250.

A number of power, timing and control signals described in greater detail in the above-incorporated, commonly assigned, '434 and '752 patents are supplied by the digital controller/timer circuit 132 to the demodulators 150 and 250 to initiate and power the operation of the physiologic and reference sensors 20 and 220 and to selectively read out the absolute and reference pressure and temperature signals. The ADC/MUX circuit 142 digitizes absolute analog signals $V_{prsabs}$ and $V_{tempabs}$ received by digital controller/timer circuit 132 from absolute signal demodulator 150 for temporary storage by microcomputer circuit 114. Similarly, ADC/MUX circuit 142 digitizes reference analog signals $V_{prsref}$ and $V_{temref}$ received by digital controller/timer circuit 132 from reference signal demodulator 250 for temporary storage by microcomputer circuit 114. The digitized reference analog signals $V_{prsref}$ and $V_{temref}$ are subtracted from the digitized absolute analog signals $V_{prsabs}$ and $V_{tempabs}$ to derive the digitized relative pressure and temperature signals $V_{prsrel}$ and $V_{temprel}$ that are used to control the delivery of a therapy and/or stored in RAM 124 for later uplink telemetry out to external programmer 400. Such data transmitted out through RF TX/RX circuit 136 during an uplink telemetry transmission is also multiplexed by ADC/MUX circuit 142.

As configured in solid lines in FIG. 2, the IMD 100 functions as an implantable physiologic signal sensor, specifically for monitoring and periodically storing digitized relative blood pressure and temperature signals $V_{prsrel}$ and $V_{temprel}$ and optionally storing digitized patient activity level and EGM samples. The, IMD 100 may also optionally include a further lead connector for connection with further lead for implantation in a right heart chamber having an exposed unipolar distal electrode from which an electrogram (EGM) may be derived. The further lead may also have an oxygen or other blood gas sensor module, a pH sensor, or the like in the distal segment of the lead. A suitable oxygen sensor module bearing lead and oxygen sensor demodulator is disclosed in commonly assigned U.S. Pat. No. 4,750,495, incorporated herein by reference.

The modification of the IMD 100 could also include a unipolar cardiac EGM sensing electrode located at the distal tip of lead 12 as disclosed in the above-incorporated '434 and '752 patents. Or two or more sense electrodes can be disposed on the housing of IMD 100 as in the MEDTRONIC® Reveal implantable heart monitor. In either case, such EGM sense electrodes are coupled with sense amplifiers within input/output circuit 112. In that optional configuration, the EGM signal may be employed to identify the onset of a cardiac depolarization in each heart cycle and automatically initiate either the monitoring and storage operations or simply initiate the storage of the data derived by continuous monitoring which would otherwise not be stored. Alternatively, the monitored parameters, including patient activity, blood pressure and temperature, blood pH, blood oxygen or other gas saturation level and EGM, can be continuously monitored. Alternatively, in any monitoring configuration, monitoring can be initiated and enabled by the patient when the patient feels the onset of a cardiac arrhythmia. In this case, the monitoring may be initiated by application of a magnet over the IMD 100 to close a reed switch or magnetic sensor (not shown). A date and time event marker is stored with the relative physiologic data set, and the data set is retained for later telemetry out to the external programmer 400 and examination by the physician or other medical attendant.

Figure 3:
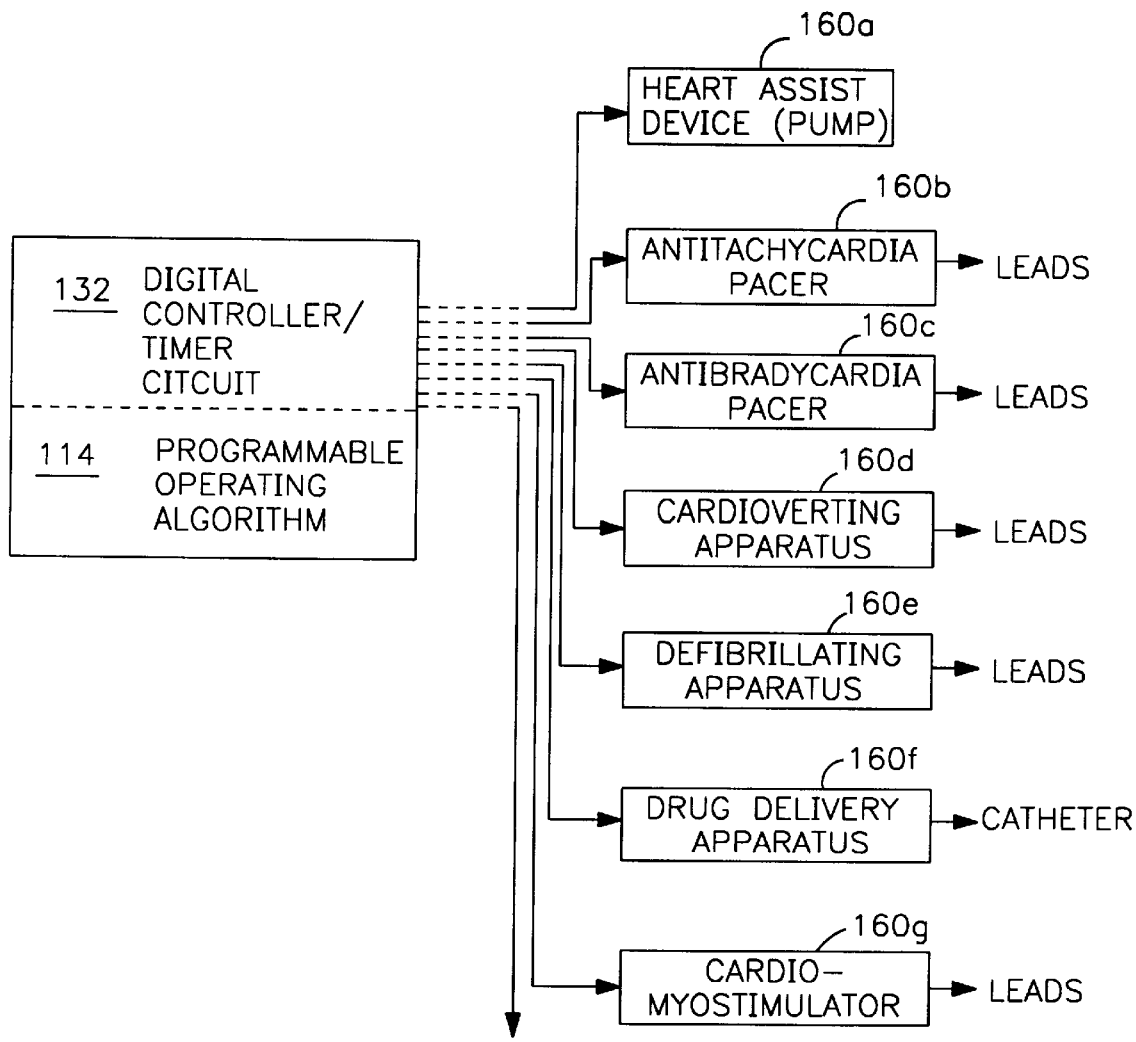
FIG. 3 is an expanded block diagram of exemplary cardiac therapy delivery apparatus usable in conjunction with the implantable system of FIGS. 1 and 2.

In the context of an implantable cardiac therapy delivery device, the relative physiologic signal values, namely the relative blood pressure and/or temperature signal values are used in an operating algorithm stored in RAM/ROM chip 128 to control the delivery of the therapy. A therapy delivery system 160 is schematically illustrated In FIG. 2, and exemplary cardiac therapy delivery apparatus usable in conjunction with the implantable, programmable blood pressure and temperature monitor of FIGS. 1 and 2 are illustrated in FIG. 3. The IMD 100 may be configured to operate an implantable heart assist device or pump 160a implanted in patients awaiting a heart transplant operation. In this case, the derived relative blood pressure and/or temperature values may be used to modulate the action of the pump to maintain adequate cardiac output. Or it may be configured to include any one or a combination of the anti-tachycardia pacer 160b, anti-bradycardia pacer 160c, cardioverting apparatus 160d and/or defibrillating apparatus 160e having suitable leads and electrodes extending from the implantable therapy delivery medical device 100 to the patient's heart 10 for sensing the EGM and delivering pacing pulses or cardioversion/defibrillation shocks. In these cases, the derived relative blood pressure and/or temperature values may be used to modulate the pacing rate to maintain adequate cardiac output or to augment the detection of malignant tachyarrythmias and fibrillation or flutter. Or the IMD may be configured as a MEDTRONIC® Transform™ Cardiomyostimulator 160g having suitable leads extending to the patient's heart and the skeletal muscle wrapped about the heart to sense the cardiac EGM and time delivery of the muscle stimulation pulses. Again, the derived relative blood pressure and/or temperature values may be used to modulate the muscle stimulation rate to maintain adequate cardiac output. Alternatively, the IMD 100 may be configured to include the drug delivery apparatus 160f which is coupled to a suitable catheter extending to the patient's heart 10 or vascular system to directly deliver drugs to treat hypertension, for example. In each case, a programmable operating algorithm governs the operation of the device and the control of the delivery of the therapy as a function of the relative physiologic signal value, e.g. relative blood pressure and/or blood temperature. As suggested in the above-incorporated '505, '859, and '987 patents, these therapy delivery apparatus 160a–160g may be combined in various combinations as necessary to treat a given patient.

Figure 4:
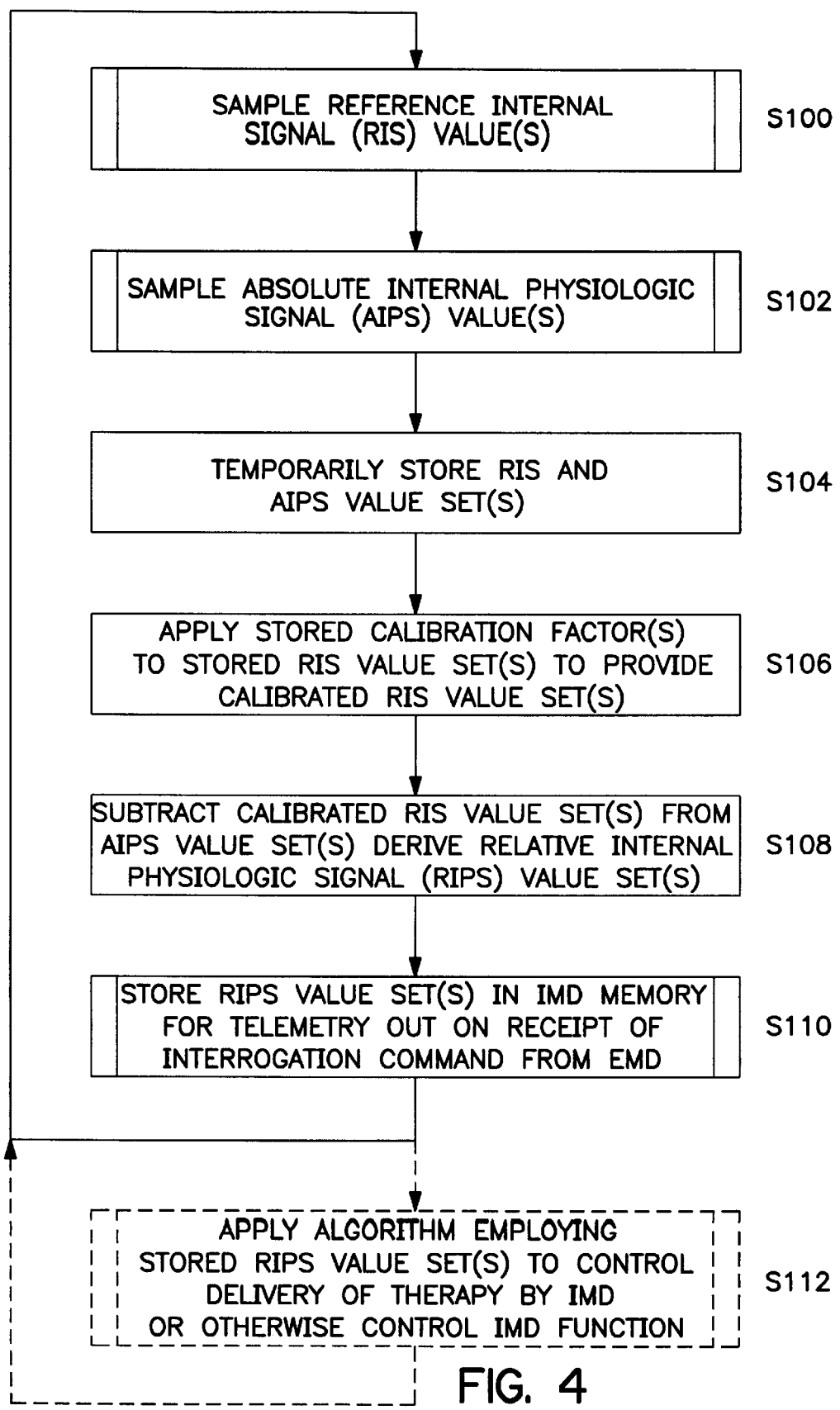
FIG. 4 is a flow chart illustrating the operation of the system of FIGS. 1 and 2, particularly for deriving the reference signal value, specifically reference pressure and/or body temperature, and combining it with the sensed absolute physiologic signal value, specifically blood pressure and/or temperature.

FIG. 4 is a flow chart illustrating the operation of the system of FIGS. 1 and 2, particularly for deriving reference internal signal (RIS) values, specifically reference internal pressure related to barometric pressure and/or body internal temperature and combining the RIS values with the sensed absolute internal physiologic signal (AIPS) values, specifically blood pressure and/or temperature, and deriving the relative internal physiologic signal (RIPS) values. In step S100, the RIS values are continuously or periodically derived at a programmed sample rate that is related to the type of monitor or therapy delivery device. Similarly, the AIPs values are continuously or periodically derived at the same or a differing sample rate that is related to the type of monitor or therapy delivery device in step S102. Typically, the sample rate of the more rapidly changing AIPS values will be greater than the sample rate of the more slowly changing RIS values The sampled RIS and AIPS values are temporarily stored between each sample event in step S104.

It is anticipated that it may be necessary to periodically calibrate the reference barometric pressure/ambient temperature sensor 220 as tissue growth or accumulation of deposits around it occur or as local inflammation at the implantation site affect temperature and pressure. Moreover, the ability of the reference barometric pressure/ambient temperature sensor 220 to accurately measure static barometric pressure/body temperature and to track relatively rapid changes in barometric pressure/body temperature will also depend on the implantation site, the thickness of the overlying tissue and other factors.

Consequently, it is believed necessary to provide some manner of providing calibration factors for periodically calibrating the RIS value(s), that is offsetting the $V_{tempref}$ and $V_{prsref}$ values, so that the calibrated $V_{tempref}$ and $V_{prsref}$ values remain unchanged whenever the patient is subjected to the same barometric pressure and exhibits the same body temperature. Such calibration would take place at least upon implantation of the IMD 100 and then whenever the performance of the IMD is assessed in a follow-up session when the contents of the memory storing the RIPS value data set is interrogated and telemetered out to the external programmer 400. The calibration routine is shown in FIG. 5 and described below.

In step S106, the calibration factor(s) are applied to the temporarily stored RIS values(s) to provide the calibrated RIS value(s). In step S108, the relative internal physiologic signal (RIPS) value(s), that is relative blood pressure/ temperature in the preferred embodiment, are calculated by subtracting the calibrated RIS value(s) from the temporarily stored AIPS value(s). The RIPS value(s) are stored in IMD memory in step S110. The RIPS value(s) are also used to control the delivery of a therapy in step S112 in the case where the IMD includes a therapy delivery system 160.

Figure 5:
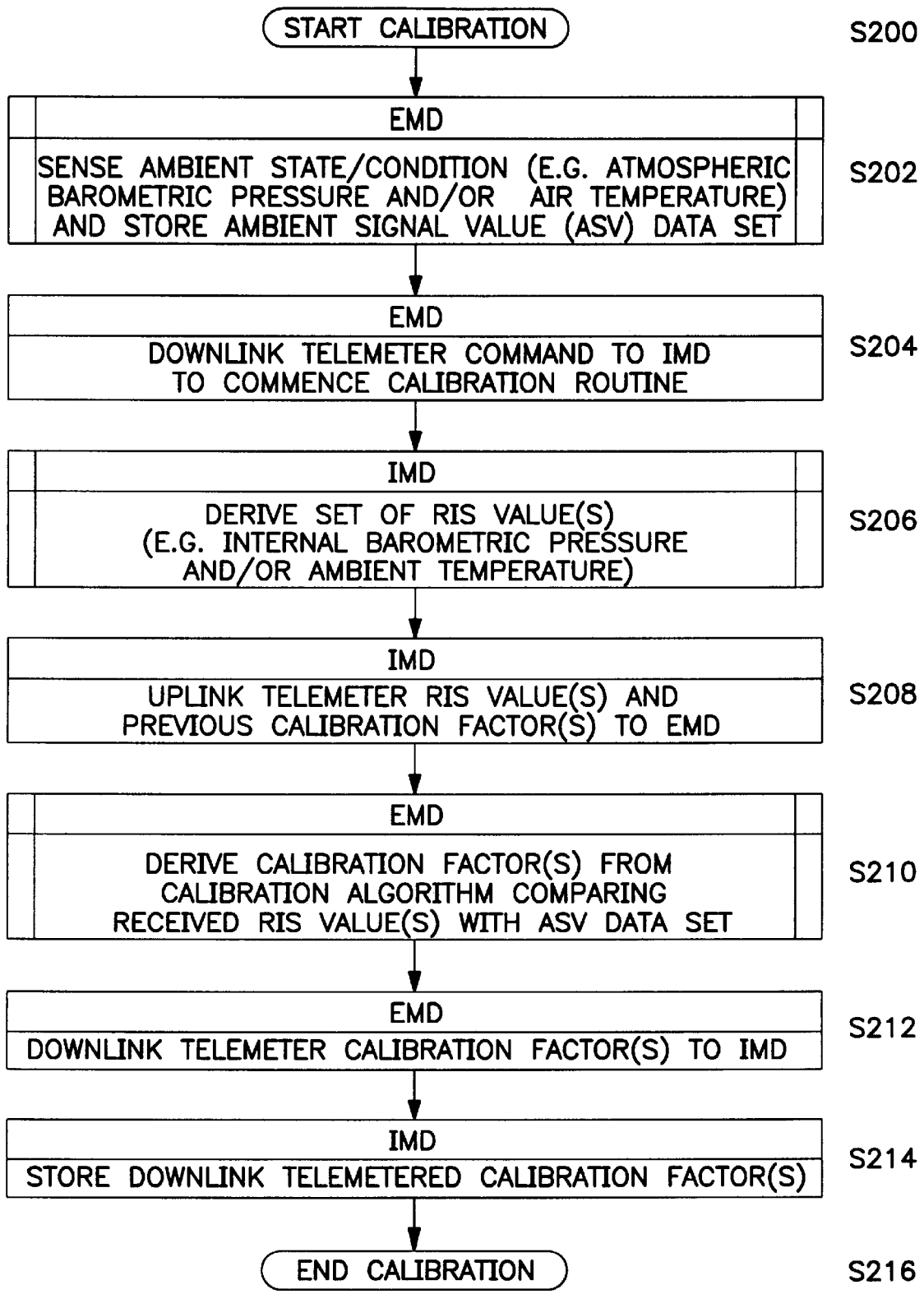
FIG. 5 is a simplified flow chart setting forth the steps of periodically reading out the reference blood pressure and/or temperature data stored in the IMD memory and calibrating the reference pressure and/or temperature sensors to provide the calibration factor(s) for use in FIG. 4.

FIG. 5 is a simplified flow chart setting forth the steps of periodically reading out the reference blood pressure and/or temperature data stored in the IMD memory and calibrating the reference pressure and/or temperature sensors to provide the calibration factor(s) for use in step S106. Calibration is started in step S200 in a telemetry session, and the external medical device (EMD) or programmer 400 in FIG. 1 senses barometric pressure and the patient's body temperature using external calibrated barometric pressure and body temperature sensor 410 and derives and stores an ambient signal value(s) set in step S202. In step S204, a command is downlink telemetered to the IMD to commence the calibration routine, and the IMD responds in step S206 by deriving a set of RIS value(s). In step S208, the derived set of RIS value(s) and the previously derived and stored calibration factor(s) are uplink telemetered to the EMD. In step S210, the EMD derives the calibration factor(s) from the uplink telemetered RIS value(s) set and the ASV data. The derived new calibration factor(s) can be compared to the previously derived calibration factor(s) by the physician and a decision is made to downlink telemeter the new calibration factor(s) to the IMD in step S212. The new calibration factor(s) are stored in the IMD in substitution for the previous calibration factor(s) in step S214, and the calibration routine is concluded in step S216.

Figure 7:
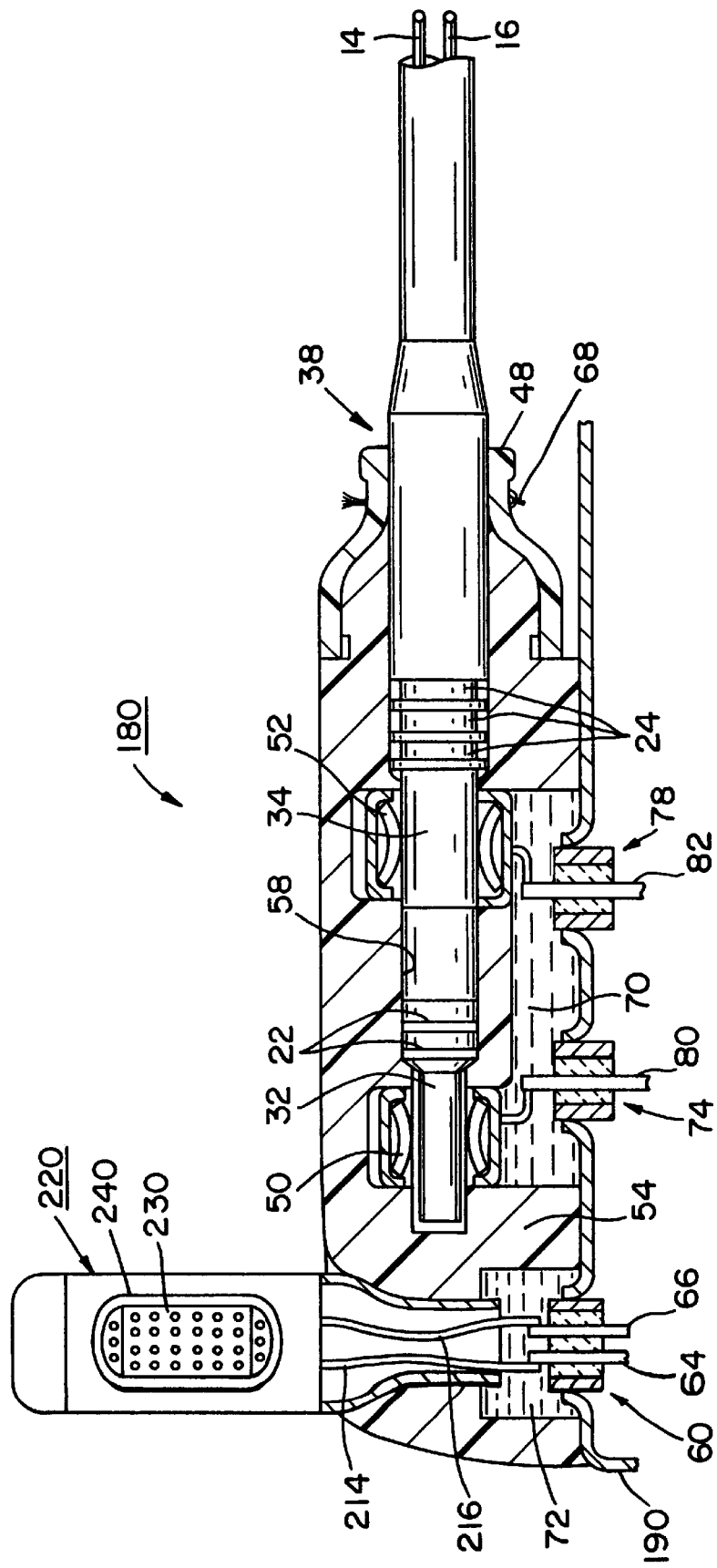
FIG. 7 is a cross-section view of a reference pressure and/or temperature sensor of the type employed in the embodiment of FIG. 6 formed within the connector module and extending from a feedthrough in the hermetically sealed enclosure of the IMD of FIGS. 1 and 2.

FIGS. 6 and 7 are views of two manners of connecting the reference pressure and temperature sensor 220 with the IMD 100 of FIGS. 1 and 2. FIG. 6 is a plan view of both reference and absolute blood pressure and/or temperature sensor bearing leads 212 and 12, respectively, extending from a connector module 180 of the IMD 100 of FIGS. 1 and 2. FIG. 7 is a cross-section view of a further reference pressure and/or temperature sensor 220 of the type employed in the embodiment of FIG. 6 formed within and extending from a feedthrough 60 in the connector module 180 of the IMD 100 of FIGS. 1 and 2.

In FIG. 6, the connector module 180 includes a pair of bores adapted to receive the typical bipolar, in-line proximal connector ends 38 and 238 of the lead 12 and lead body 212 in a manner shown in FIG. 7. As shown in FIG. 2, the lead body 212 includes the first and second lead conductors 214 and 216 that extend between electrical connections made with the reference pressure and temperature sensor 220 and the proximal connector pin 232 and connector ring 234. The proximal connector pin 232 and connector ring 234 are adapted to be received in the connector blocks of the connector module that are in turn coupled to feedthrough pins extending in feedthroughs mounted in the hermetically sealed enclosure wall encasing the components of the IMD device 100 illustrated in FIG. 2 in a manner well known in the art. The proximal connector pin 232 and connector ring 234 are separated from one another by a non-conductive spacer 235 and proximal sealing rings 222. Distal sealing rings 224 are also provided distally to the connector ring 224 for sealing the connector module bore receiving the lead connector end 238 in a manner well known in the art.

Lead 12 is constructed in the manner described in the above-incorporated '434 and '752 patents. The lead 20 thus includes a distal tip electrode 26 that can be used to sense the EGM and to apply pacing pulses to the heart. The lead connector end 38 of lead 12 is constructed in a similar manner to couple the first and second lead conductors 14 and 16 between the proximal connector pin 32 and connector ring 34 with terminals of the absolute pressure and temperature sensor 20 and the distal electrode 26.

The reference pressure and temperature sensor 220 at the end of lead body 212 is constructed in the same manner as the absolute pressure and temperature sensor described in the above-incorporated '434 and '752 patents. Lead body 212 is relatively short, and the reference pressure and temperature sensor 220 is extended to a location close to the IMD and in a pocket under the patient's skin where it is in contact with or surrounded by body fluids. Preferably, a fluid pervious grill or shroud 230 surrounds the reference pressure and temperature sensor 220 in order to allow body fluid but to prevent body tissue from bearing against the flexible diaphragm 240 of the reference pressure and temperature sensor 220. The holes preferably are one millimeter in diameter give or take about "½ millimeter to avoid tissue ingrowth. This is in keeping with the work of Dr. Guyton who emplanted empty chambers with fluid communications holes subcutaneously to enable local fluid pressure measurements to be made through a syringe pushed into such chambers. (See A. Guyton "Techniques in measurement of tissue fluid pressure and lymph flow" Cardiovascualr Physiology (1973) pages 1–27, incorporated herein by this reference.)

The shroud 230 can be formed of a silicon rubber or plastic sieve or metal screen material having a number of fluid permeating bores or slots formed in it to admit body fluid into contact with the diaphragm 240. The shroud 230 can be somewhat deformable but preferably resists being collapsed against the diaphragm 240 when the shroud 230 and the reference pressure and temperature sensor 220 are fitted into the pocket. Generally the cover or shroud can be quite stiff or rigid, similar to the rigidity of a "Wiffle" (™—Wiffle Ball, Inc, Shelton Conn., USA) ball or harder. By using a stiff screen apart from pressure on the sensor surface, this sensor surface is in physical contact with body fluid such as lymph but the fluid pressure is not affected by muscle movement.

In FIG. 7, the reference pressure and/or temperature sensor 220 of the type employed in the embodiment of FIG. 6 is formed with the connector module 180 and extends from a feedthrough 60 extending through the hermetic sealing enclosure wall 190 and through a portion of the encapsulate 54 forming the connector module 180 The feedthrough 60 is formed with feedthrough pins 64 and 66 that are electrically connected at one end with the conductors 214 and 216 and with the VDD and IN and OUT terminals of reference signal demodulator 250 of FIG. 2 as described above. A metal screen shroud 230 is fitted over the diaphragm 240 to prevent body tissue from contacting it as described above.

The reference pressure and/or temperature sensor 220 extends out of the encapsulating material 54 because of its relatively large size and elongated tubular shape and because it is oriented to extend at right angles to the elongated bore 58 that receives the proximal connector end 38 of the absolute pressure and/or temperature sensor lead 12. This depicted orientation is merely exemplary of one way of mounting the reference pressure and/or temperature sensor 220, and it will be understood that it could be aligned to extend alongside the elongated bore 58 with the diaphragm 240 oriented outward from the side of the connector module 180. In that configuration, screen or shroud 230 could be mounted to extend across an opening in the encapsulant 54 over the diaphragm 240.

The connector module 180 is formed of the encapsulant 54 to provide the elongated bore 58 for receiving the connector end 38 and for making electrical contact of the flexible connector receptacles 50 and 52 with the connector pin 32 and the connector ring 34 in a manner well known in the art. When the connector end 38 is seated in the bore 54, the sealing rings 22 and 24 are compressed in the elongated bore 54, and a suture 68 can be tied around a boot 48 to further seal the bore 58 from the ingress of body fluids in a manner well known in the art. The flexible connector receptacles 50 and 52 are electrically connected to feedthrough pins 80 and 82 of feedthroughs 74 and 78 extending through the enclosure wall 190. The feedthrough pins 80 and 82 are connected with the VDD and IN and OUT terminals of absolute signal demodulator 150 of FIG. 2 as described above. Cavities 70 and 72 provide access to make the depicted electrical connections of the feedthrough pins 80, 82 and 64, 66 respectively, as described above and are then filled with silicon rubber in a manner well known in the art.

The present invention can be practiced using reference barometric and absolute blood pressure sensors and appropriate drive circuits of other types than the capacitive sensors and demodulator circuits described above. For example, micro-machined semiconductor strain gauge pressure transducers or piezoresistive strain gauge transducers of the type shown in the above-incorporated '296 patent or '755 patent could be employed. The absolute pressure sensor leads of the first embodiment of the '296 patent or of the '755 patent can be employed as the lead 12 and absolute pressure sensor 20 with appropriate power supply and readout circuitry substituted for the demodulator 150 of FIG. 2. Similarly, the pressure sensors of the first embodiment of the '296 patent or of the '755 patent can be employed as the reference pressure sensors 220 with the appropriate power supply and readout circuitry substituted for the demodulator 250 of FIG. 2.

Figure 8:
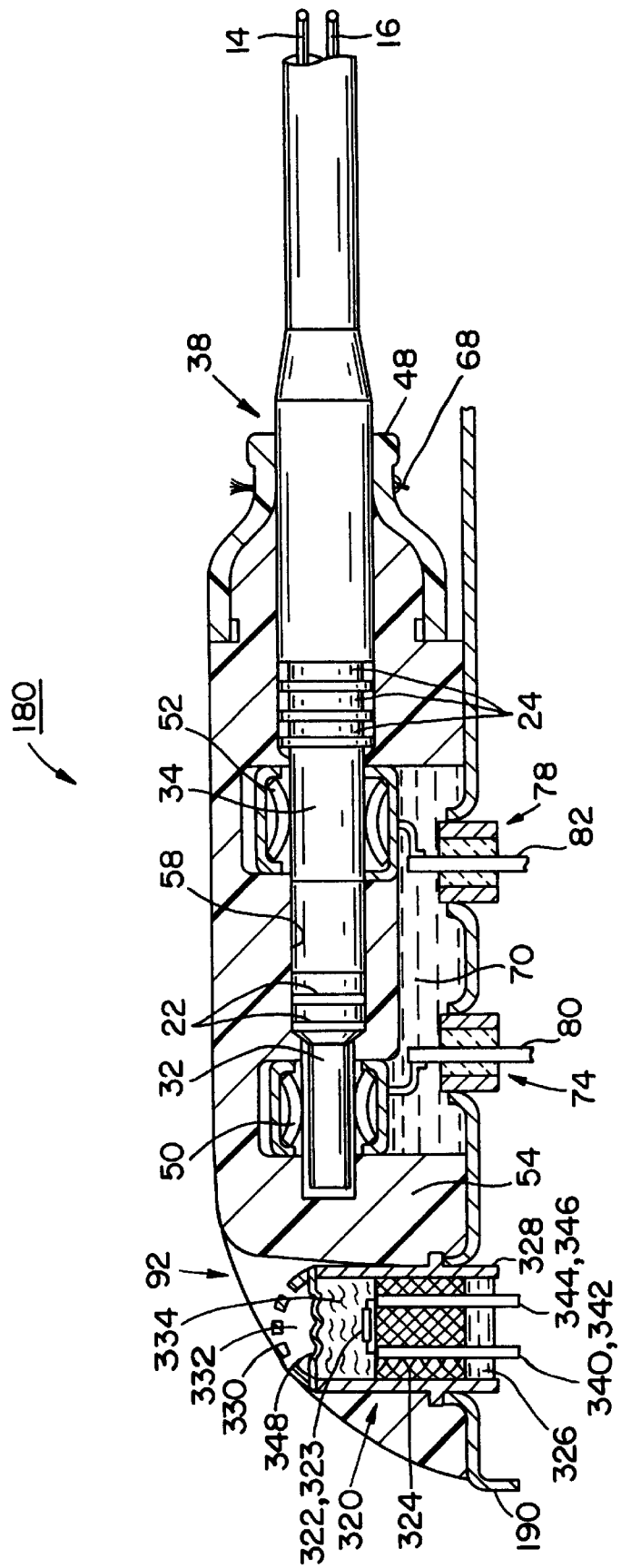
FIG. 8 is a cross-section view of a reference pressure and/or temperature sensor of a further configuration formed within the connector module integrally with a multi-pin feedthrough in the hermetically sealed enclosure of the IMD of FIGS. 1 and 2.

FIG. 8 is a cross-section view of the use of a reference pressure sensor 320 of a further configuration formed within recess 92 in the encapsulant 54 of the connector module 180 that is similar to the first embodiment absolute pressure sensor disclosed in the above-incorporated '296 patent. This reference pressure sensor 320 can be employed with a pressure sensor lead of the type corresponding to the first embodiment pressure sensor lead disclosed in the above-incorporated '296 patent. Or it can be used with the pressure and temperature sensor lead disclosed in the above incorporated '434 and '752 patents to provide a reference pressure.

Figure 9:
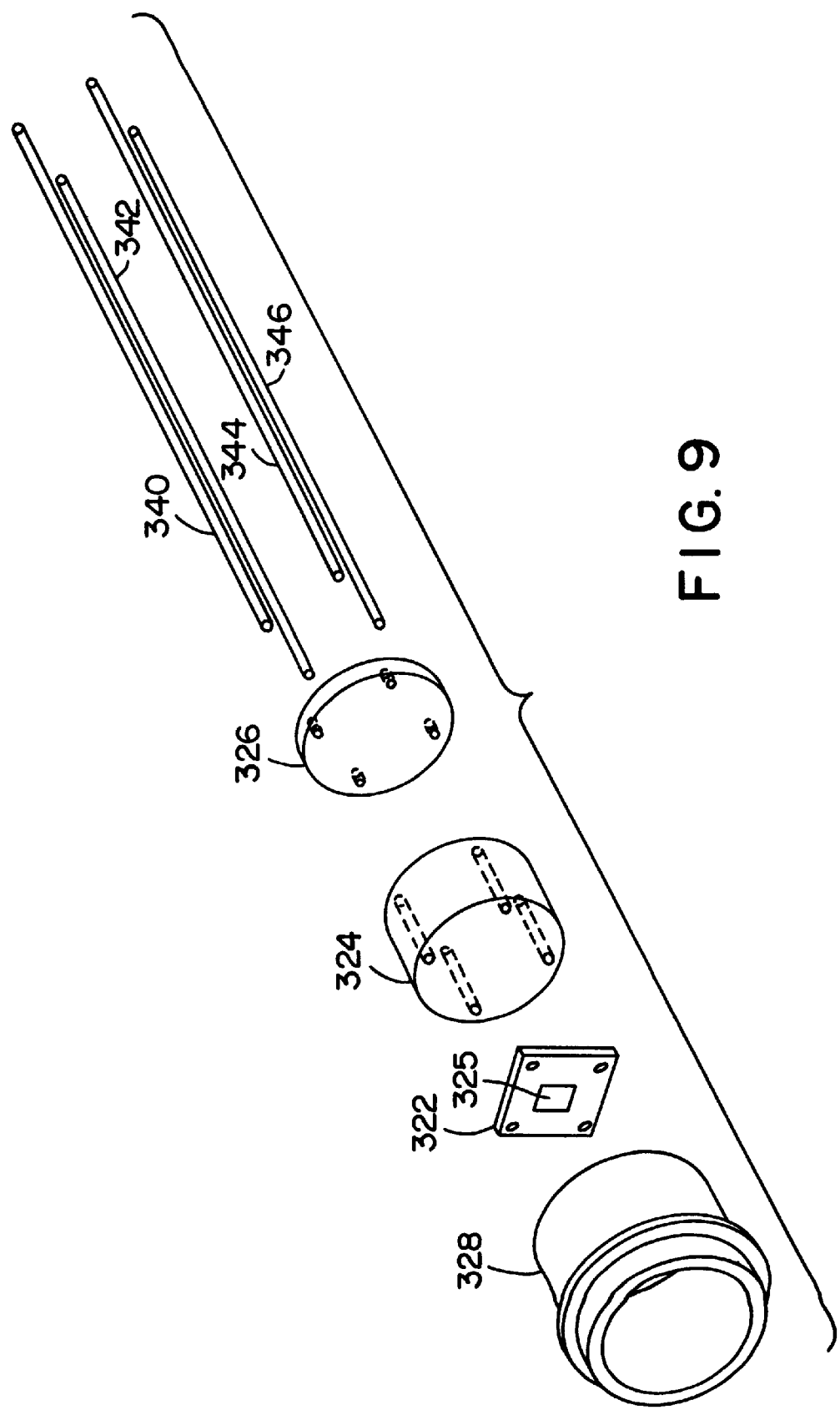
FIG. 9 is an exploded perspective view of the components of the reference pressure and/or temperature sensor and feedthrough assembly of FIG. 8.

The reference pressure and/or temperature sensor 320 includes a micro-machined, semiconductor, pressure transducer 322 mounted to the surface of a sealing glass disk 324 located within a ferrule 328. The pressure sensor has four electrical terminals that are electrically connected to four noble metal feedthrough pins 340, 342, 344, 346 that extend through the sealing glass disk 324 and through a further barrier glass disk 326 into the interior of the enclosure wall 190. The pressure transducer 322 is preferably a silicon micromachined sensor type that is formed on a semiconductor chip die that is about 0.075 inches on each side. The other sensors could of course be used. The sensor has four terminals that can be wire bonded to the ends of the four noble metal feedthrough pins 340, 342, 344, 346 that extend through the sealing glass disk 324. After the electrical connections are made, the sealing disk surface, the wire bonds and the exposed areas of the pressure transducer 322 except for the movable sensing element or diaphragm 323 of the pressuretransducer 322 are preferably covered with epoxy. FIG. 9 is an exploded perspective view of these components of the reference pressure and/or temperature sensor and feedthrough assembly shown in FIG. 8.

As shown in FIG. 8, the micro-machined, semiconductor, pressure transducer 322 mounted to the surface of a sealing glass disk 324 is located in a chamber 434 enclosed by a diaphragm 348 and the cylindrical ferrule 328 that is preferably filled with a silicone oil or the like in the manner described in the above-incorporated '096 patent. In this case, an outer, perforated grill or shroud 330 is mounted to the circular end of the tubular ferrule 328 and the circular rim of the diaphragm 348 to protect the diaphragm 348 from contact with tissue while allowing fluid ingress into the outer chamber 332. Ambient pressure changes of the body fluid under the skin and in the outer chamber 332, which relate to changes in barometric pressure, are applied to the diaphragm 348 which moves and causes the oil within inner chamber 434 to apply pressure to the movable diaphragm or element 323 of the pressure transducer 322.

It will be understood that certain pressure transducers 322 can be used wherein the area of the movable diaphragm or element 323 can simply be coated with a layer of silicone rubber or the like, and the chamber 34 and diaphragm 348 can be dispensed with if preferred.

Various different sensors could be used and another highly preferred one would be of the type disclosed in U.S. Pat. No. 5,564,434 incorporated herein by this reference. The entire capsule holding the sensor can be easily mounted to the body of the IMD and the electrical connections fed through the via a commonly available feedthrough.

In these embodiments, it is assumed that the reference internal pressure and ambient temperature sensor is capable of responding to changes in barometric pressure reflected through the layer of skin and tissue overlying it in at least a consistently proportional fashion and reasonably rapidly. It is also possible to locate the reference pressure and/or temperature sensors 220 or 320 illustrated in FIGS. 6–8 within a percutaneous access device of the type that is implanted in the patient's skin so that the diaphragm 240 or 348 is directly exposed to the atmosphere. In such a location, ambient pressure and/or body temperature is directly measured, and the response to any changes is rapid. In one variation, the percutaneous access device houses the reference pressure and/or temperature sensor 220 or 320, and it is connected to the connector module 180 as in FIG. 6. In a second variation, an air column is maintained between the atmosphere and the diaphragm 240 or 348 of the reference pressure and/or temperature sensor 220 or 320, respectively, mounted on or in the connector module 180 as in FIGS. 7 and 8.

Figure 10:
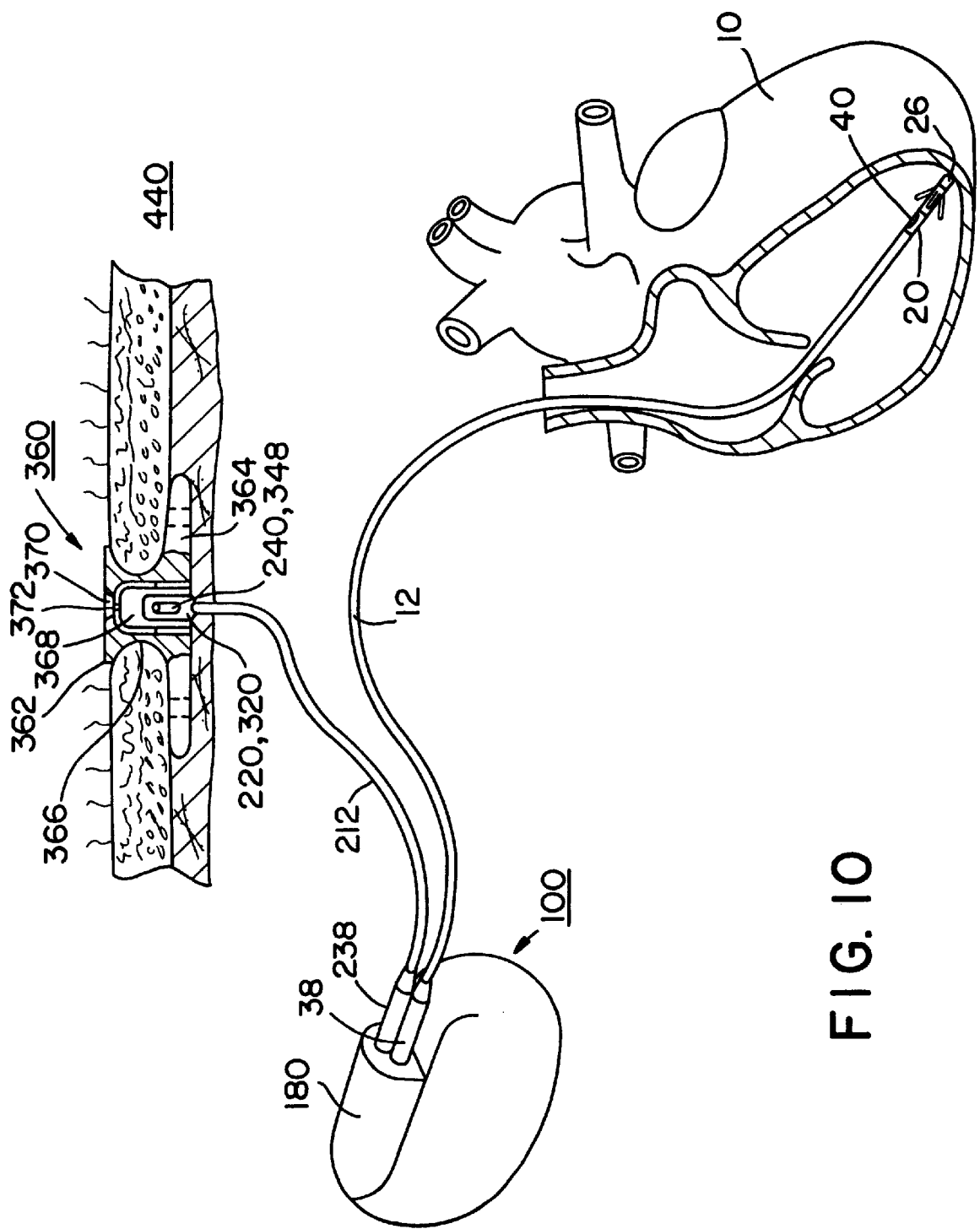
FIG. 10 is a schematic illustration of a further embodiment of the invention locating the reference pressure and/or temperature sensor in a percutaneous access device so that the diaphragm is exposed directly to the atmosphere.
Figure 11:
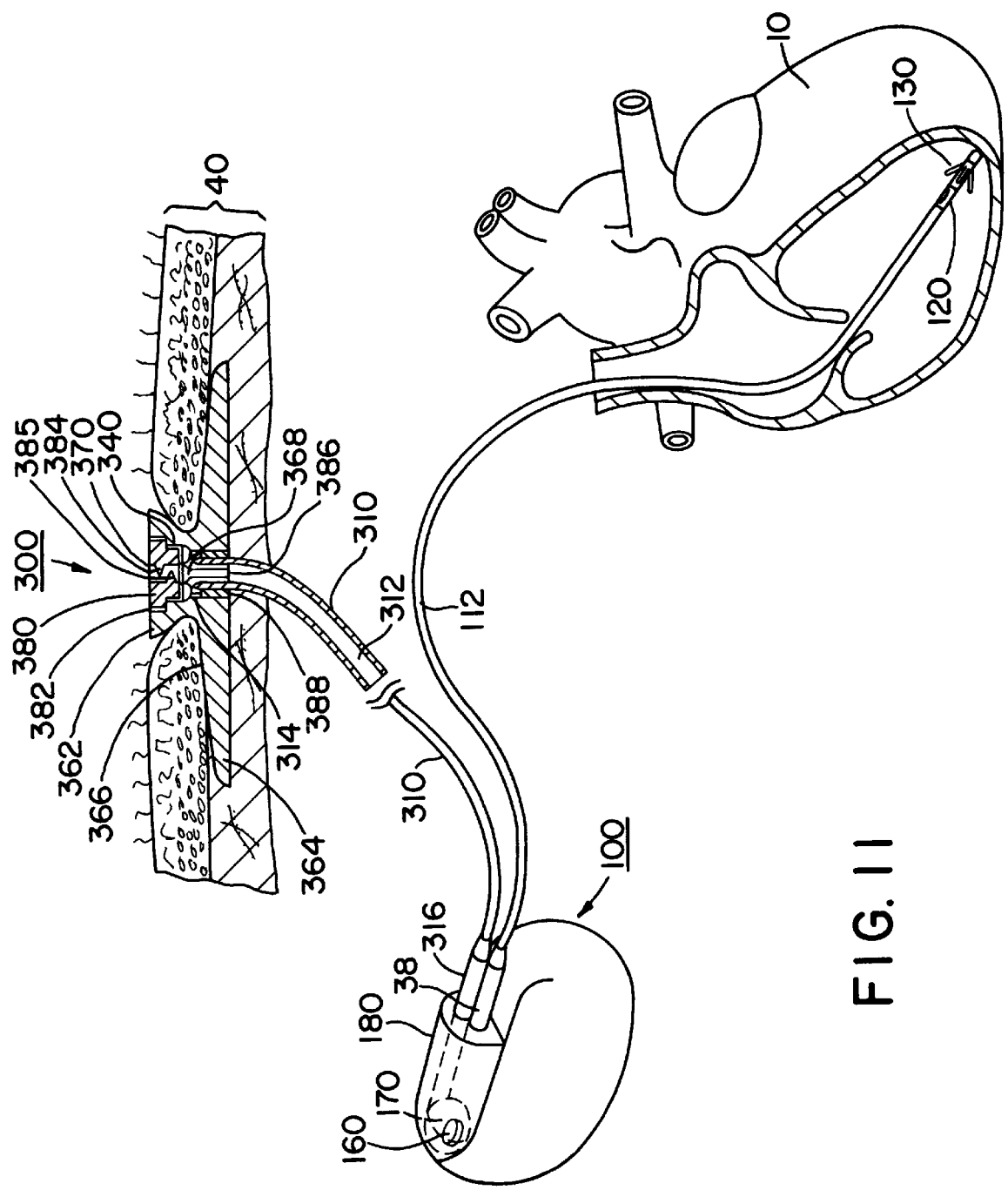
FIG. 11 is a schematic illustration of a still further embodiment of the invention locating the reference pressure and/or temperature sensor in or on the connector module of the IMD and extending a catheter to the percutaneous access device so that the diaphragm is exposed directly to the atmosphere through the air in the catheter lumen.

FIGS. 10 and 11 schematically illustrate these variations of such a system employing a percutaneous access device 360 that is chronically implanted in the patient's skin and subcutaneous tissue layer 440. The percutaneous access device 360 is formed like a bobbin, having a plate-like exterior flange 362 and a plate-like interior flange 364 coupled together by a cylindrical side wall 366 surrounding a tubular chamber 368. Such percutaneous access devices are well known in the prior art and are employed as vascular access devices for periodic catheterization of blood vessels, as electrode terminals or as drug delivery access ports or other devices for obtaining chronic access within the body or to allow body fluids or waste to be expelled. Such percutaneous access devices and are formed of a bio-compatible material, e.g., pyrolytic carbon, that is surface treated in a variety of ways to encourage tissue growth around the exterior surface of the side wall 366 and typically through porous surfaces or holes in the interior flange 364. The upper and lower flanges 362 and 364 are also shaped to discourage expulsion of the percutaneous access device 360 from the skin and subcutaneous tissue layer 440. The upper flange 362 extends to the exterior of the patient's skin and subcutaneous tissue layer 440 and above the air chamber 368, and an air vent 370 from the air chamber 368 is formed through it.

The air vent 370 is preferably covered by a porous, waterproof, fabric cover 372 formed of Gore-Tex® or the like that allows air to pass therethrough while inhibiting the passage of moisture therethrough and into the air chamber 368 as also disclosed in the above-referenced, commonly assigned (P-7687) application.

In the first variation depicted in FIG. 10, the reference pressure and/or temperature sensors 220 or 320 is mounted into chamber 368, and the lead body 212 extends between it and a connector bore of the connector module 180. It will be understood that the diaphragm 240 or 348 is separated from the interior surface of side wall 366 and is exposed to air in chamber 368 that passes through the porous cover 370 and the air vent(s) 362. The lead body 212 extends from the percutaneous access device to the proximal connector end 238 that is fitted into a bore of the connector module 180 in the same manner as described in reference to FIG. 6 and that the proximal connector end 38 is attached to connector module 180 as illustrated in FIG. 7. Thus, this system functions in the same manner as the systems described above with reference to FIGS. 2–5 optionally including the calibration routine of FIG. 6 employing the reference pressure and/or temperature sensor 220 or 320.

In the second variation depicted in FIG. 11, the reference pressure and/or temperature sensor 220 or 320 is mounted on or in the connector module 180 in the manners depicted in FIGS. 7 or 8 such that the diaphragm 240 or 348 is disposed in an air chamber enclosed within the connector module 180 that is open to one of the connector bores. It will be understood that FIG. 11 is intended to illustrate the interconnection of the percutaneous access device 360 with any manner of mounting the reference pressure and/or temperature sensor 220 or 320 on or in the connector module 180 within an air chamber that is impervious to fluid penetration when a connection is made with it as described below.

In this embodiment, the air vent 370 is formed in a cylindrical stopper 380 that fills a cylindrical bore 382 in the upper flange 362. The air vent 370 in the cylindrical stopper 380 includes laterally extending baffles 384 to prevent the insertion of a needle or the like through it and the porous cover 372. The cylindrical stopper 380 is sealed into the cylindrical bore 382 during assembly, and the porous cover 372 is trapped between the planar interior surfaces of the cylindrical stopper 380 and the cylindrical bore 382. In this way, moisture and particulate contaminants are prevented from entering the air chamber 368, but air pressure within the air chamber 368 is at barometric pressure outside the patient's skin and tissue layer 440.

A catheter 512 is provided that encloses a catheter lumen 514 extending between a proximal catheter connector end 538 and a distal catheter end 540. The distal catheter end 540 is coupled to the air chamber 368 of the percutaneous access device 360. This coupling is effected by flaring and fitting the distal catheter end 540 over a tube 386 extending downwardly in a cylindrical bore 388 so that the catheter lumen 514 is aligned with a tube lumen forming the air chamber 368. A press ring or adhesive or both fill the space within cylindrical bore 388 to mechanically hold the distal catheter end 540 in position and to seal chamber 368 from ingress of moisture or contaminants.

The air chamber 368 is empty and vented through the air vent 370 and porous cover 372, and so an air column extends from the air chamber 368 through the catheter lumen 514 and to an air chamber 170 enclosing the reference pressure and/or temperature sensor 220 or 320 mounted on or in the connector module. As illustrated in FIG. 11, the proximal catheter connector end 538 is fitted into a bore of the connector module 180 and sealed there to prevent the ingress of body fluids into the air column provided by catheter lumen 514. It will be understood that the proximal catheter connector end 538 could also surround the reference pressure and/or temperature sensor 220 projecting outward of the connector module 180 as depicted in FIG. 7 or could mate with the recess 92 or ferrule 328 of FIG. 8. In all such cases, a strong, fluid impervious connection is made preferably at manufacture so that the catheter 512 is permanently attached at its proximal end to the connector module 180 and at its distal end to the percutaneous access device 360. Thus, this system functions in the same manner as the systems described above with reference to FIGS. 2–5, optionally including the calibration routine of FIG. 6 employing the reference pressure and/or temperature sensor 220 or 320.

Figure 12A:
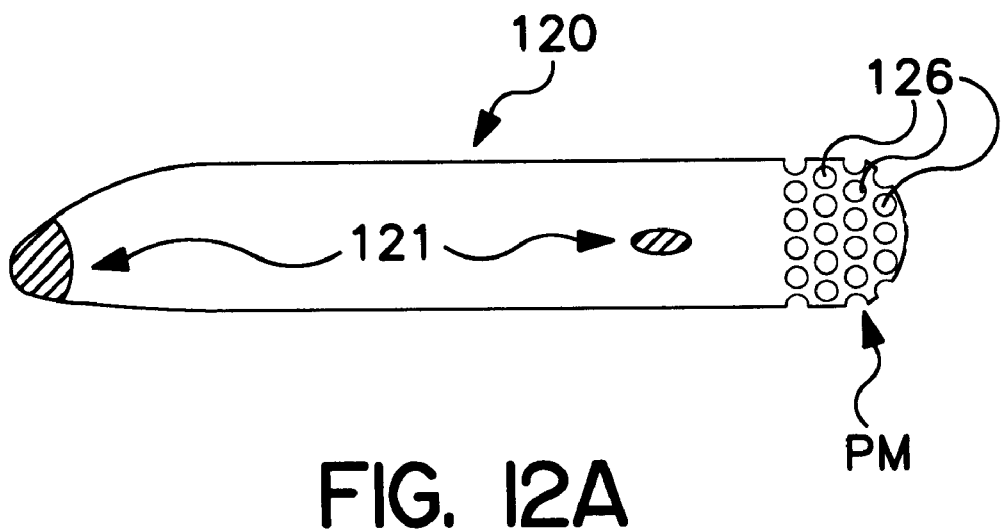
FIGS. 12a and 12b are alternative side views of a sealed and open device, respectively in accord with an embodiment of this invention.
Figure 12B:
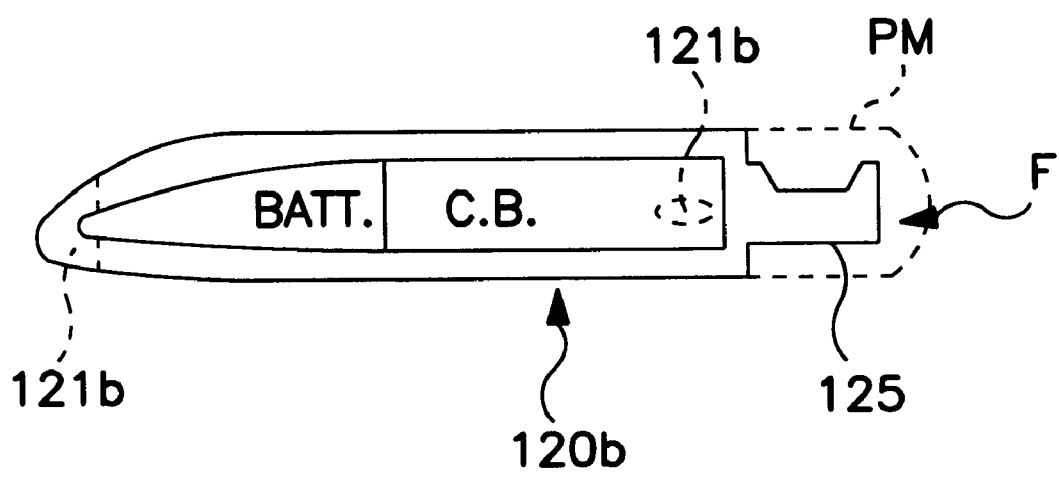

FIGS. 12a and 12b describe a simplified IMD having a pressure sensor module PM integrally formed therewith, housing a pressure sensor unit 125 in which the pressure seven is mounter. The area in the Module is filled either with bodily fluids for F or with medical adhesive gell F so as to transmit local pressure through the holes 126 to the pressure sensor. The device 120/1206 may be implanted anywhere a local pressure needs to be sensed and the device can telemeter out data via telemetry circuitry on the circuit board C.b. Other data gathering communications activity can be accomplished with eternal electrodes 121 in a manner known to those of ordinary skill in the medical device art.

The pressure data recorded by an independent implant such as device 120/120b can be coordinated in this application above, or in other ways for calibration reference and comparative measurement purposes.

Essentially, by adding supportive circuitry to a currently available IMD like Medtronic REVEAL (™) along with a pressure module, a functioning pressure and ECG recording device may be created which would look like the FIGS. 12a and b device.

The description of the preceding specific embodiments satisfy the statutory requirements for description and are therefore to be understood as illustrative of only a limited set of the many ways in which the invention may be practiced. It is to be understood, therefore, that other expedients known to those of skill in the art or disclosed herein may be employed without departing from the abstract of invention which is only limited by the following appended claims.

What is claimed is:

1. An implantable pressure module for substantially immovable attachment to an implantable medical device having a free space within a module housing and a pressure sensor mounted firmly within said free space in said module housing, and wherein said pressure sensor is mounted firmly but spaced apart from an opening in said module housing, said opening to said free space comprising a porous opening having a shroud covering the opening over with a plurality of holes formed into said shroud of a size approximately 1 millimeter in diameter such that bodily fluids may communicate their pressure into said free space, and said housing having a conductor means for electrically connecting said pressure sensor through said housing and into circuitry within said medical device housing via a fixed attachment point between said module housing and said implantable medical device.

2. The implantable pressure module of claim 1 and further comprising a circuit for recording pressure sensor measurements made by said pressure sensor, wherein said circuit is fixedly attached to an outer surface of said implantable medical device and communicated into said medical device via said conductor means.

* * * * *